US011320356B2

(12) United States Patent
Endo et al.

(10) Patent No.: US 11,320,356 B2
(45) Date of Patent: May 3, 2022

(54) METHOD FOR ESTIMATING NUMBER OF MICROPARTICLES IN SAMPLE

(71) Applicants:METAWATER CO., LTD., Tokyo (JP); Takuro Endo, Tokyo (JP)

(72) Inventors: Takuro Endo, Tokyo (JP); Kyungju Kim, Tokyo (JP); Dabide Yamaguchi, Tokyo (JP)

(73) Assignees: Takuro Endo, Tokyo (JP); METAWATER CO., LTD., Tokyo (JP)

( * ) Notice: Subject to any disclaimer, the term of this patent is extended or adjusted under 35 U.S.C. 154(b) by 33 days.

(21) Appl. No.: 16/093,566

(22) PCT Filed: Apr. 17, 2017

(86) PCT No.: PCT/JP2017/015448
§ 371 (c)(1),
(2) Date: Oct. 12, 2018

(87) PCT Pub. No.: WO2017/183600
PCT Pub. Date: Oct. 26, 2017

(65) Prior Publication Data
US 2019/0204200 A1   Jul. 4, 2019

(30) Foreign Application Priority Data

Apr. 19, 2016   (JP) .............................. JP2016-083778

(51) Int. Cl.
*G01N 15/06* (2006.01)
*G01N 15/14* (2006.01)
(Continued)

(52) U.S. Cl.
CPC ............... *G01N 15/06* (2013.01); *C12Q 1/06* (2013.01); *G01N 15/14* (2013.01);
(Continued)

(58) Field of Classification Search
CPC ........ G01N 15/06; G01N 21/64; G01N 33/18; C12Q 1/06; Y02A 50/30
See application file for complete search history.

(56) References Cited

U.S. PATENT DOCUMENTS

2006/0154309 A1* 7/2006 Takahashi ........ G01N 33/57492
435/7.23
2006/0211082 A1 9/2006 McCoy

FOREIGN PATENT DOCUMENTS

JP   H03-238340 A    10/1991
JP   H03238340 A  *  10/1991
(Continued)

OTHER PUBLICATIONS

Communication dated Nov. 27, 2019, from the European Patent Office in counterpart European Application No. 17785938.6.
(Continued)

*Primary Examiner* — Tracy Vivlemore
*Assistant Examiner* — Nam P Nguyen
(74) *Attorney, Agent, or Firm* — ArentFox Schiff LLP

(57) ABSTRACT

Providing a method of estimating the number of microparticles such as microorganisms in a sample, without performing complicated operations. The method comprises counting by constant flow the number of target microorganisms contained in the sample at a predetermined flow rate, sectioning measurement data obtained as a result of the constant flow counting into a predetermined number of sections by a predetermined unit time for a section, counting the number of sections in which microorganisms are detected and the number of sections in which they are not detected, in the predetermined number of sections; and estimating the number of microorganisms in the sample, by a statistical method from the flow rate of the sample in the constant flow counting step, the predetermined number of sections and the
(Continued)

predetermined unit time in the sectioning step, and the number of sections in which microorganisms are detected in the counting step.

6 Claims, 1 Drawing Sheet

(51) Int. Cl.
    *G01N 33/569*    (2006.01)
    *G01N 21/64*     (2006.01)
    *C12Q 1/06*      (2006.01)
    *G01N 33/536*    (2006.01)
    *G01N 33/18*     (2006.01)

(52) U.S. Cl.
    CPC ......... *G01N 15/1429* (2013.01); *G01N 21/64* (2013.01); *G01N 33/18* (2013.01); *G01N 33/536* (2013.01); *G01N 33/569* (2013.01); *G01N 2015/0693* (2013.01); *Y02A 50/30* (2018.01)

(56) References Cited

FOREIGN PATENT DOCUMENTS

| | | |
|---|---|---|
| JP | H09-72842 A | 3/1997 |
| JP | H11-94727 A | 4/1999 |
| JP | 2008-532551 A | 8/2008 |
| JP | 2013-178134 A | 9/2013 |
| WO | WO 2015/187783 A1 | 12/2015 |

OTHER PUBLICATIONS

International Search Report and Written Opinion dated Jul. 18, 2017 issued in International Application No. PCT/JP2017/015448.
Oblinger, J.L. et al., "Understanding and Teaching the Most Probable Number Technique" Food Science Department: University of Florida, Gainsville, FL; Published in Journal of Milk and Food Technology, vol. 38, No. 9, pp. 540-545 (Sep. 1975).

\* cited by examiner

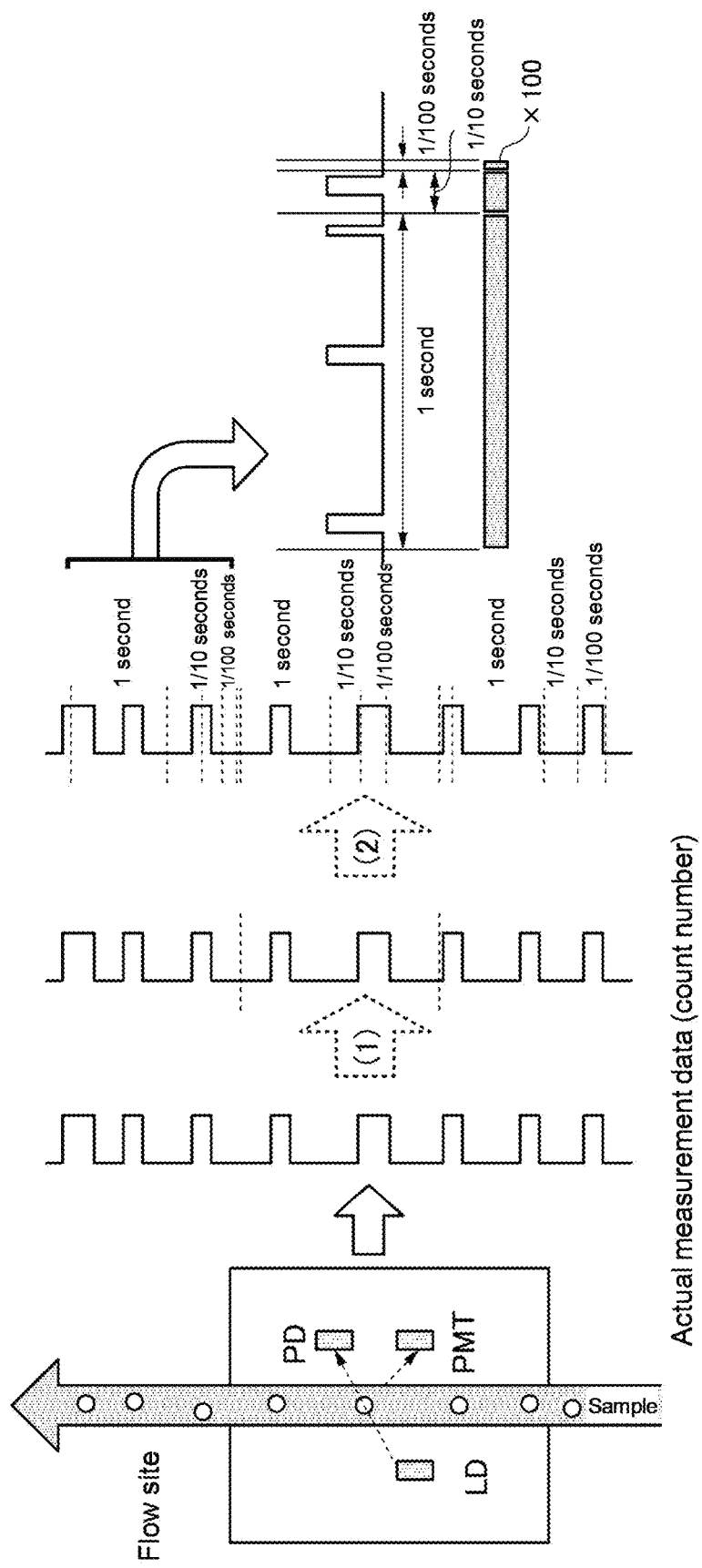

METHOD FOR ESTIMATING NUMBER OF MICROPARTICLES IN SAMPLE

CROSS-REFERENCE TO RELATED APPLICATIONS

This application is a 35 U.S.C. § 371 National Phase of PCT Application No. PCT/JP2017/015448 filed Apr. 17, 2017, which claims priority to Japanese Application No. JP 2016-083778 filed Apr. 19, 2016. The disclosures of these prior applications hereby incorporated by reference herein.

TECHNICAL FIELD

The present invention relates to a method of estimating the number of microparticles in a sample, which enables rapid and convenient estimation of the number of the microparticles such as microorganisms in water without performing complicated treatment (e.g. cultivation, etc. in case of microorganisms).

BACKGROUND ART

A wide variety of pathogenic microorganisms which adversely affect human bodies are known. Among these pathogenic microorganisms, microorganisms spreading through tap water are also known. Severe water quality standards have been determined for tap water served for drinking, so that infectious diseases and the like do not occur through tap water widely supplied to houses. Therefore, in the field of clean water treatment, it is necessary to confirm the number of pathogenic microorganisms per unit volume of clean water (hereinafter referred to as "concentration") at the stage before supplying clean water as tap water. Clean water as tap water may be supplied only after a concentration of pathogenic microorganisms in the clean water is below the reference value.

Incidentally, when determining a concentration of microorganisms in water, the water as a sample is diluted at a predetermined magnification, and microorganisms in the diluted sample are cultivated, and then, the number of the microorganisms in the sample before cultivation is estimated, and finally the concentration of the microorganisms in the sample before dilution is estimated. However, this method takes time for cultivation, and it will be extremely difficult to estimate a concentration of a microorganism which artificial cultivation is difficult, because a step of cultivating a microorganism in a sample is required as an essential step.

In order to solve such problems, for example, Patent Literature 1 discloses a method of rapidly qualifying *Legionella* bacteria in a sample, the method comprising: (a) providing an absorbent medium comprising nutrients for cultivating *Legionella* bacteria, and at least one agent to selectively inhibit the growth of non-*Legionella* microorganisms; (b) contacting the absorbent medium with the sample for a predetermined amount of time; (c) incubating the absorbent medium at a temperature in the range of about 30° C. to about 45° C. for a period of about 6 hours to about 48 hours; (d) detecting growth of *Legionella* bacteria in the absorbent medium with a detection reagent; and (e) quantifying the amount of viable *Legionella* bacteria in the sample.

CITATION LIST

Patent Literature

Patent Literature 1: JP 2008-532551

SUMMARY OF THE INVENTION

Technical Problem

However, even the method described in Patent Literature 1 takes a considerable time for cultivation, because the method includes the step of cultivating microorganisms as an essential step. In particular, in the method described in Patent Literature 1, an agent to selectively inhibit the growth of non-*Legionella* microorganisms is added to the absorbent medium, and thus, in some cases, the absorbent medium must be prepared when required, and qualifying *Legionella* bacteria takes a lot of labor and trouble. Accordingly, the present invention has been made in view of the above problems, and an object of the present invention is to provide a method of estimating the number of microparticles such as microorganisms in a sample, which can be operated quickly and conveniently without performing complicated treatment when estimating the number of the microparticles.

Solution to the Problem

The inventors of the present invention have conducted extensive research in view of the above problems. As a result, the present inventors have found that the above problems can be solved by counting the number of microparticles contained in a sample at a predetermined flow rate by counting means such as flow cytometry; sectioning measurement data indicating a relationship between elapsed time and the number of detected microparticles, into a predetermined number of sections by a predetermined unit time for a section; counting the number of sections in which the microparticles are detected and the number of sections in which the microparticles are not detected; and estimating the number of the microparticles in the sample, by a statistical method from the above flow rate, the predetermined number of sections, the predetermined unit time, and the number of sections in which the microparticles are detected. Thus, the present inventors have accomplished the present invention. Specifically, the present invention provides the following.

(1) The first aspect of the present invention is, a method of estimating the number of microparticles in a sample, comprising: a constant flow counting step of counting by constant flow the number of the target microparticles contained in the sample at a predetermined flow rate; a sectioning step of sectioning measurement data obtained as a result of the constant flow counting, indicating a relationship between elapsed time and the number of detected microparticles, into a predetermined number of sections by a predetermined unit time for a section; a section number counting step of counting the number of sections in which the microparticles are detected and the number of sections in which the microparticles are not detected, in the predetermined number of sections; and a concentration calculating step of estimating the number of the microparticles in the sample, by a statistical method from the flow rate of the sample in the constant flow counting step, the predetermined number of sections and the predetermined unit time in the sectioning step, and the number of sections in which the microparticles are detected in the section number counting step.

(2) The second aspect of the present invention is, the method according to (1), wherein the predetermined unit time in the sectioning step is determined, so that the number of sections in which the microparticles are not detected in the section number counting step is 1 or more.

(3) The third aspect of the present invention is, the method according to (1) or (2), wherein the statistical method is a most probable number method.

(4) The fourth aspect of the present invention is, the method according to (3), wherein in the sectioning step, the measurement data are sectioned into two or more predetermined number of rows of sections by two or more predetermined unit times, and in the concentration calculating step, the number of the microparticles in the sample is estimated, by a most probable number method from the flow rate of the sample in the constant flow counting step, the predetermined number of sections and the two or more predetermined unit times in the sectioning step, and the number of sections according to each of the unit times in which the microparticles are detected in the section number counting step.

(5) The fifth aspect of the present invention is, the method according to any one of (1) to (4), wherein the microparticles are microorganisms, and a fluorescent labeled antibody that binds to an antigen on a cell surface of the microorganisms is added to the sample, and in the constant flow counting step, the number of the microparticles in the sample is counted by measuring fluorescence of a fluorescent substance labeling the antibody.

(6) The sixth aspect of the present invention is, the method according to any one of (1) to (4), wherein in the constant flow counting step, the number of the microparticles in the sample is counted by a light scattering measurement.

Advantageous Effects of the Invention

In the method of the present invention, the number of microparticles such as microorganisms or the like is measured from a sample flowing at a constant flow rate by flow cytometry or the like. Such constant flow counting can detect presence of microparticles in one particle unit (in one cell unit in case of microorganisms). Thus, it is possible to count the number of the microparticles contained in the sample without performing complicated treatment such as cultivation and the like in case of microorganisms. It is also possible to count the number in one cell unit or in one particle unit even in microorganisms or microparticles or the like which cannot be cultivated. Further, in the present invention, the number of the microparticles is estimated by a statistical method from the flow rate in the constant flow counting step, the predetermined number of sections and the predetermined unit time in the sectioning step, and the number of sections in which the microparticles are detected in the section number counting step, so that statistically reliable number of the microparticles can be estimated without measuring the number of the microparticles using a large amount of samples.

BRIEF DESCRIPTION OF THE DRAWINGS

FIG. 1 shows a drawing for explaining an outline of the method of the present invention.

DESCRIPTION OF THE INVENTION

FIG. 1 shows a drawing for explaining an outline of the method of the present invention. Hereinafter, embodiments for carrying out the present invention are explained in detail with reference to the drawing.

<Method of Estimating the Number of Microparticles in a Sample>

The method of the present invention is a method of estimating the number of microparticles in a sample, comprising a constant flow counting step, a sectioning step, a section number counting step, and a concentration calculating step. Each step is explained in detail below.

[Constant Flow Counting Step]

The constant flow counting step of the first step in the method of the present invention, is a step of counting by constant flow the number of the target microparticles contained in a sample at a predetermined flow rate by counting means such as flow cytometry or a microparticle counter or the like. Here, a sample to be subjected to the method of the present invention includes raw water, clear water, sewage, industrial water, industrial waste water and the like, and is not particularly limited, but the method of the present invention is preferably used to estimate the number of microorganisms in a sample in raw water or clear water.

In addition, microparticles to be subjected to the method of the present invention include various pathogenic or non-pathogenic microorganisms, polystyrene latex (PSL), metallic beads, (artificial) glass beads, blood cells in a blood sample, and the like. Among these, it is particularly preferable to apply the present invention to estimate the number of pathogenic microorganisms.

In the present invention, the constant flow counting is performed preferably by flow cytometry, and thus, the final volume of the sample to be measured is generally at least 1 mL or more, preferably 1 mL or more and 20 mL or less. In this case, the sample to be measured may be concentrated by a conventionally known method, and when concentrated, the final volume of the sample to be measured indicates the volume after concentration.

(Flow Cytometry)

Flow cytometry preferably used in the present invention, is a method of optically detecting individual very fine particles in the state that the particles are dispersed in a fluid, which is flowed at a constant flow rate by infinitesimal amount of flow. Flow cytometry is generally performed by using a flow cytometer equipped with a flow path for distributing a fluid, a light emitting part (LD) provided on one side of the flow path, and a light receiving part (PD) and a detector (PMT) provided on the other side.

Then, the light emitting part and the light receiving part of the flow cytometer are provided on a straight line passing through one point on the flow path. When microparticles such as microorganisms pass through the one point on the flow path, a light is interrupted at the light receiving part, and a light of the same wavelength as or longer wavelength than one of the light emitted from the light emitting part reaches the detector and is detected by light scattering measurement or fluorescence measurement. Thereby, the flow cytometer detects presence of particles in the fluid.

A flow cytometer that can be used in the method of the present invention, is not particularly limited, and a general flow cytometer can be used without limitation. A specific example is CyAn ADP manufactured by Backman Coulter.

(Pretreatment of Sample)

In the present invention, a sample to be subjected to the constant flow counting step may be subjected to pretreatment in advance or may not be pretreated at all. Examples of such pretreatment include a concentration step, a separation step, a purification step and the like of a sample raw solution. Furthermore, in case of detecting microorganisms as microparticles, examples of the pretreatment include staining with a fluorescent labeled antibody or a fluorescent reagent, which is performed when microorganisms are detected by an immunofluorescent antibody method or a fluorescent staining method. Examples of the fluorescent labeled antibodies include an antibody or the like which specifically binds to an antigen specifically present on a cell surface of the target microorganisms to be measured. In addition, the fluorescent reagents include a chemical substance or the like which specifically binds to a specific chemical substance on a cell surface of or within the target microorganisms to be measured. Furthermore, nucleic acid hybridization methods such as FISH (Fluorescence In Situ Hybridization) may also be used for fluorescent labeling of microorganisms. In this case, microorganisms may be labeled by using a nucleic acid fragment labeled with a fluorescent substance or a radioactive substance. Here, when an immunofluorescent antibody method, a fluorescent staining method, or a nucleic acid hybridization method is performed on the microorganisms, optionally the microorganisms may be fixed and a surfactant treatment or the like may be performed. The fluorescent labeled antibodies and the fluorescent reagents that can be used for the above mentioned pretreatment are not particularly limited. For example, in case of intending to detect *Cryptosporidium* or *Giardia*, the fluorescent labeled antibodies and the fluorescent reagents include ARK Checker, R-phycoerythrin (PE) labeled antibody, FITC labeled antibody, Cy3 labeled antibody, as well as PI, SYTO9, SYBR (registered trademark) Green and the like as a fluorescent dye capable of staining a nucleic acid.

(Flow Rate)

In the present invention, for example, when the number of the microparticles contained in a sample is counted by constant flow by flow cytometry, flow rate of the sample flowing in a flow path in a flow cytometer is not particularly limited. It is preferably, for example, 1 μL/sec or more and 30 μL/sec or less, and more preferably 10 μL/sec or more and 20 μL/sec or less. By setting the flow rate of the sample flowing in the flow path as described above, it is possible to improve efficiency of the constant flow counting step while maintaining accuracy and reliability of the measurement of the number of the microparticles at a certain level or more.

[Sectioning Step]

In the sectioning step of the second step in the method of the present invention, measurement data obtained as a result of the constant flow counting, indicating a relationship between elapsed time and the number of detected microparticles are sectioned into a predetermined number of sections by a predetermined unit time for a section. In this step, the predetermined number of sections may be the predetermined number of successive sections.

Here, the predetermined unit time for a section at the time of sectioning is not particularly limited. However, for example, the predetermined unit time for a section is preferably determined, so that volume of the sample flowing in the flow path in the flow cytometer for the predetermined unit time is a predetermined unit volume. Specifically, when the flow rate of the sample flowing in the flow path in the flow cytometer is 100 μL/sec, by setting the unit time to 1.0 second, it is possible to determine whether the target microparticle is contained in 100 μL of the sample, and by setting the unit time to $1.0 \times 10^{-1}$ seconds, it is possible to determine whether the target microparticle is contained in 10 μL of the sample, and by setting the unit time to $1.0 \times 10^{-2}$ seconds, it is possible to determine whether the target microparticle is contained in 1 μL of the sample.

The number of sections which are sectioned by a predetermined unit time for a section is not particularly limited. However, the number of sections is preferably 5 or more, and more preferably 10 or more. Increase of the number of sections enables to estimate the statistically more accurate number of microorganisms in the concentration calculating step.

When determining the predetermined unit time in the sectioning step of the present invention, the predetermined unit time is preferably determined, so that the number of sections in which the microparticles are not detected in the predetermined number of sections (e.g. 5 sections) is 1 or more. In particular, in case of sectioning the measurement data by setting only a single unit time, when the number of sections in which the microparticles are not detected is 0, the number of the microparticles in the sample may not be accurately calculated, because the number of sections in which the microparticles are detected is saturated. By setting the unit time so that the number of sections in which the microparticles are not detected is 1 or more, more accurate number of the microparticles can be calculated even when sectioning the measurement data by setting a single unit time.

[Section Number Counting Step]

In the section number counting step of the third step in the method of the present invention, the number of sections in which the microparticles are detected and the number of sections in which the microparticles are not detected, in the predetermined number of sections are counted. In the present invention, it is unnecessary to count the number of signals corresponding to the number of detected microparticles in each section. By determining whether or not an arbitrary number of signals exists in each section, the number of the microparticles can be statistically estimated in the following concentration calculating step. By adopting this technique, in particular, even in case that a plurality of signals exist in one section and peaks of the signals are overlapped, measurement data can be obtained without deteriorating accuracy of the measurement data, because the measurement date are obtained by determining whether or not a signal exists in each section.

[Concentration Calculating Step]

In the concentration calculating step of the fourth step in the method of the present invention, for example, the total amount of the sample water to be tested and the total amount of the sample water in which the microparticles are detected are obtained, from the flow rate of the sample in the constant flow counting step, the predetermined number of sections and the predetermined unit time in the sectioning step, and the number of sections in which the microparticles are detected in the section number counting step; and then, the number of the microparticles in the sample is estimated by a statistical method. By adopting this technique to estimate the number of the microparticles, a range of the numerical values having accuracy at a determined level or higher can be obtained as the number of the microparticles to be estimated, and the statistically significant number of the microparticles can be estimated.

Here, statistical methods used for estimating the number of microparticles are not particularly limited. However, it is preferable to use a most probable number method (for example, J. Milk Food Technol. Vol. 38, No. 9, Pages 540-545, September, 1975).

The most probable number method is generally a method of statistically estimating a microbial concentration of a given sample, wherein a predetermined dilution series of the given sample are prepared, and microorganisms in the diluted samples are cultivated, and a microbial concentration of a given sample before dilution is estimated from the number of positive cultivated samples per the predetermined number of the diluted samples of each dilution magnification. The operation of sectioning the measurement data of the sample by counting by constant flow at a predetermined flow rate by a predetermined unit time, and determining whether or not the microparticles are detected, corresponds to an operation of determining whether or not microorganisms (microparticles) are detected in a predetermined unit volume of a sample. Therefore, the conventional most probable number method can be applied to the present invention without performing complicated treatment such as cultivation and the like of the microorganisms when detecting the microorganisms.

In the most probable number method, a most probable number table obtained by a predetermined mathematical calculation is prepared, and the number of microorganisms is estimated from the above dilution magnification and the number of the positive cultivated samples by referring to this most probable number table. However, the present invention is not limited to such a method. The number of the macroparticles may be estimated by calculating by a mathematical/statistical method, or statistically by computer simulation or the like, from the above flow rate, the predetermined number of sections, the predetermined unit time, and the number of sections in which the microparticles are detected.

In the present invention, in the sectioning step described above, the measurement data are preferably sectioned into two or more predetermined number of rows of sections by two or more predetermined unit times, and in the concentration calculating step, the number of the microparticles in the sample is estimated, by a most probable number method from the flow rate of the sample, the predetermined number of sections and the two or more predetermined unit times in the sectioning step, and the number of sections according to each of the unit times in which the microparticles are detected in the section number counting step. More reliable estimation can be performed by sectioning into two or more predetermined number of rows of sections. Also, by using the most probable number method, appropriate estimation can be performed depending on time and cost, because accuracy at a determined level or higher is available even if there are a few sections.

Here, the above mentioned step is explained referring to FIG. 1. For example, when flow cytometry is performed at a flow rate of 100 µL/sec, at first, the measurement data is sectioned by the unit time of 2 seconds, and the obtained sections are sectioned by the unit time of 1 second, $1.0 \times 10^{-1}$ seconds and $1.0 \times 10^{-2}$ seconds respectively. Among the three sections sectioned by the unit time of 1 second, the number of sections in which microparticles are detected is recorded. Among the three sections sectioned by the unit time of $1.0 \times 10^{-1}$ seconds, the number of sections in which microparticles are detected is recorded. Among the three sections sectioned by the unit time of $1.0 \times 10^{-2}$ seconds, the number of sections in which microparticles are detected is recorded. Then, the number of the microparticles in the sample is estimated by the most probable number method, from the flow rate, the predetermined unit time and the predetermined number of sections, and the number of the sections in which the microparticles are detected.

According to the above method, statistically highly accurate and reliable number of the microorganisms can be estimated without performing complicated treatment such as cultivation and the like of the microorganisms in a sample when detecting the microorganisms. In addition, a step of cultivation of microorganisms in a sample is not necessary in the present invention, so that the present invention can apply to measurement of concentrations of not only microparticles which cannot be cultivated in the first place, but also concentrations of protozoa which artificial cultivation is difficult, including *Cryptosporidium* and *Giardia*. It is also suitable for rapid measurement of concentration of protozoa which require a long time for cultivation, like *Legionella*.

The invention claimed is:

1. A method of estimating the number of microparticles in a sample, comprising:
    a constant flow counting step of counting by constant flow the number of the target microparticles contained in the sample at a predetermined flow rate;
    a sectioning step of sectioning measurement data obtained as a result of the constant flow counting, indicating a relationship between elapsed time and the number of detected microparticles, into a predetermined number of sections by a predetermined unit time for a section, wherein the measurement data are sectioned into two or more predetermined number of rows of sections by two or more predetermined unit times;
    a section number counting step of counting the number of sections in which the microparticles are detected and the number of sections in which the microparticles are not detected, in the predetermined number of sections, wherein the number of signals corresponding to the number of detected microparticles are not counted, and wherein the number of the microparticles in the sample is counted by one of: measuring fluorescence and a light scattering measurement; and
    a concentration calculating step of estimating the number of the microparticles in the sample, by a statistical method from the flow rate of the sample in the constant flow counting step, the predetermined number of sections and the predetermined unit time in the sectioning step, and the number of sections in which the microparticles are detected in the section number counting step.

2. The method according to claim 1, wherein the predetermined unit time in the sectioning step is determined, so that the number of sections in which the microparticles are not detected in the section number counting step is 1 or more.

3. The method according to claim 1, wherein the statistical method is a most probable number method.

4. The method according to claim 3, wherein in the concentration calculating step, the number of the microparticles in the sample is estimated, by a most probable number method from the flow rate of the sample in the constant flow counting step, the predetermined number of sections and the two or more predetermined unit times in the sectioning step, and the number of sections according to each of the unit times in which the microparticles are detected in the section number counting step.

5. The method according to claim 1, wherein the microparticles are microorganisms, and a fluorescent labeled antibody that binds to an antigen on a cell surface of the microorganisms is added to the sample, and in the constant flow counting step, the number of the microparticles in the sample is counted by measuring fluorescence of a fluorescent substance labeling the antibody.

6. The method according to claim 1, wherein in the constant flow counting step, the number of the microparticles in the sample is counted by a light scattering measurement.

* * * * *